(12) United States Patent
Cao

(10) Patent No.: US 7,485,116 B2
(45) Date of Patent: Feb. 3, 2009

(54) LASER SYSTEMS, WITH A FIBER STORAGE AND DISPENSING UNIT, USEFUL IN MEDICINE AND DENTISTRY

(76) Inventor: Densen Cao, 2851 E. Durban Rd., Sandy, UT (US) 84093

( * ) Notice: Subject to any disclaimer, the term of this patent is extended or adjusted under 35 U.S.C. 154(b) by 99 days.

(21) Appl. No.: 10/947,055

(22) Filed: Sep. 22, 2004

(65) Prior Publication Data

US 2006/0064080 A1    Mar. 23, 2006

(51) Int. Cl.
*A61B 18/20* (2006.01)
(52) U.S. Cl. ........................................ 606/10
(58) Field of Classification Search ............... 606/2–19
See application file for complete search history.

(56) References Cited

U.S. PATENT DOCUMENTS

| 4,418,689 | A | * | 12/1983 | Kanazawa | 600/108 |
|---|---|---|---|---|---|
| 4,775,211 | A | * | 10/1988 | Wondrazek et al. | 385/88 |
| 4,974,793 | A | * | 12/1990 | Pinson | 244/3.12 |
| 5,290,273 | A | * | 3/1994 | Tan | 606/9 |
| 5,644,585 | A | * | 7/1997 | Mitchell et al. | 372/25 |
| 5,703,991 | A | * | 12/1997 | Izumi | 385/135 |
| 6,092,394 | A | * | 7/2000 | Backer et al. | 65/377 |
| 6,367,629 | B1 | | 4/2002 | Bautista et al. | |
| 6,504,986 | B1 | | 1/2003 | Wambeke | |
| 6,829,425 | B2 | | 12/2004 | Barthel et al. | |
| 6,845,207 | B2 | | 1/2005 | Schray | |
| 2005/0203496 | A1 | * | 9/2005 | Ritchie et al. | 606/15 |

* cited by examiner

*Primary Examiner*—Henry M. Johnson, III
(74) *Attorney, Agent, or Firm*—Geoffrey E. Dobbin

(57) ABSTRACT

A laser system useful in medicine or dentistry that includes a removable fiber module that manages fiber dispensing to avoid damage to or waste of fiber.

21 Claims, 14 Drawing Sheets

D1 > D2

LASER SYSTEMS, WITH A FIBER STORAGE AND DISPENSING UNIT, USEFUL IN MEDICINE AND DENTISTRY

I. BACKGROUND

A. Field

Medical and dental surgical and therapeutic laser systems are disclosed herein.

B. Background

Various light sources have been used in medicine and dentistry for surgery and therapeutics.

II. SUMMARY

Semiconductor-based laser systems are provided that are useful for tissue cutting and therapeutics in medical and dental treatment environments.

III. BRIEF DESCRIPTION OF THE DRAWINGS

FIG. 1b depicts an example of a back panel of the laser system of FIG. 1a.

FIG. 1c depicts exemplary interior components of a laser system such as depicted in FIG. 1a.

IV. DETAILED DESCRIPTION

Semiconductor laser systems, such as those depicted herein, have many surgical and therapeutic applications in medicine and dentistry. They can be used for many purposes, including but not limited to surgical cutting, coagulation, bacteria reduction, tissue burning, tissue therapy, drug delivery, dermatology treatment, tooth whitening, and other uses. Various laser system components are described, any of which may be used singly or in combination in various desire laser systems. The following are examples that illustrate several concepts and structures regarding semiconductor laser systems.

V. General Description of a Laser System

Detailed description of laser system is as follows.

A. Enclosure or Box

Figure 1A:
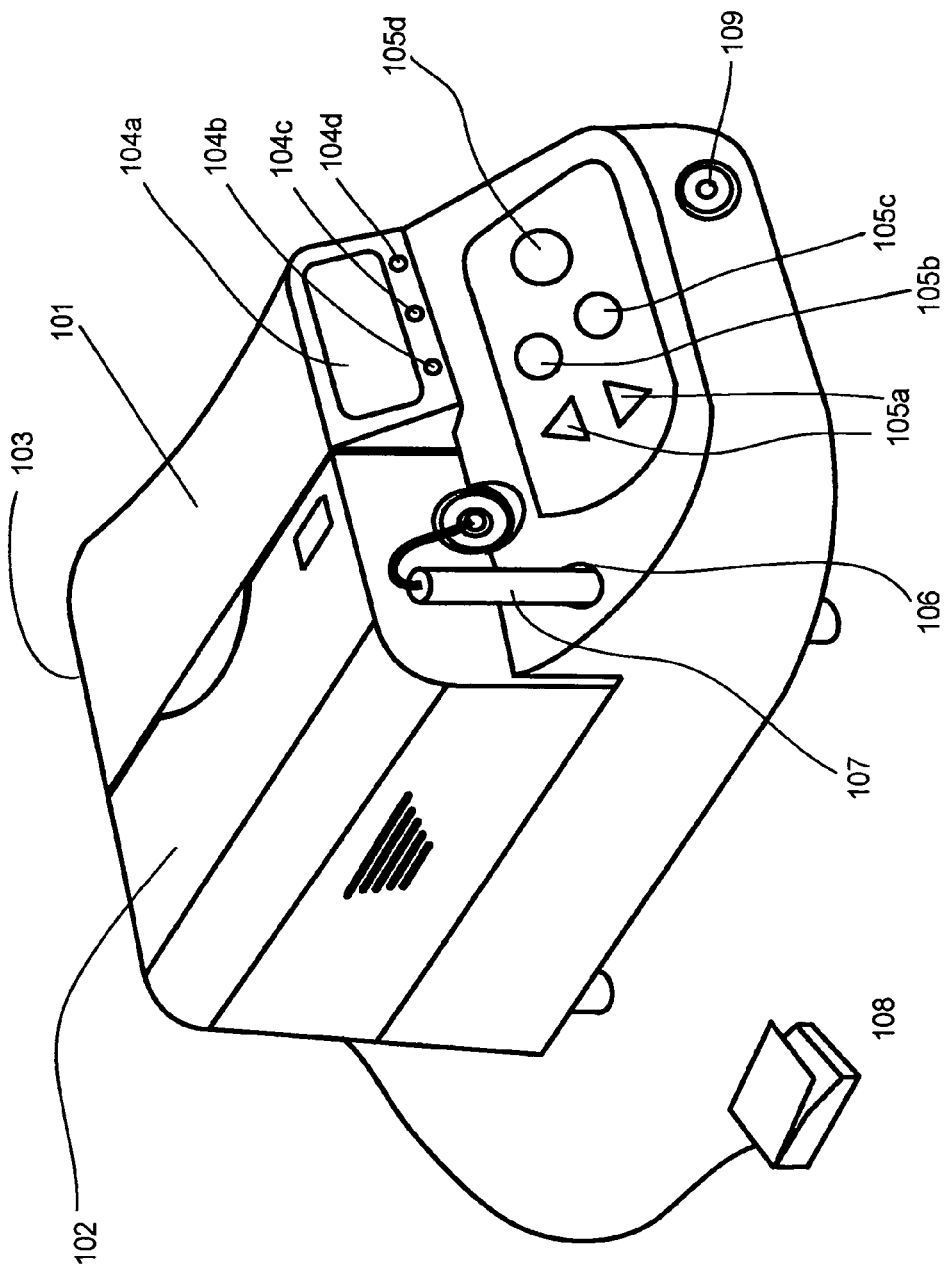
FIG. 1a depicts a front view of a laser system, such as that which can be used for medical or dental surgical and therapeutic purposes.

Depicted in FIG. 1a, an enclosure or box 101 may be provided to contain most of the components of the laser system. The enclosure 101 provides protection for the laser system, permits ventilation of interior components as needed, accommodates portability, and accommodates convenient physical positioning. The dimensions of an example of enclosure 101 may be as desired, such as about 6 inches in height, 10 inches in width, and 12 inches in depth, or less, although other dimensions can be used as desired. The box 101 can be made of plastic, metal, alloy or other suitable materials. The box 101 can be any desired shape, and may include aesthetic contouring or decorative materials on its exterior.

Attached to the enclosure box, there is a fiber cartridge 102 to attach to the box to manage the fiber delivery. Detailed description of fiber cartridge will be in following sections. A rear panel 103 (only one edge of the rear panel 103 is visible) containing electrical input will be described in FIG. 1b.

A display panel 104a is in the enclosure box to display laser operation information. A panel meter 104a to display the laser output power with indicator lights 104b, 104c, and 104d to display the laser status. One LED display is used to indicate laser beam emission status. When that LED is lit, this indicates that laser light is being emitted from the laser system. When no light is emitted from the LED, it indicates that no laser light is being emitted from the laser system. Another LED displays the continuous wave (CW) or Pulse operation status. When that LED is lit, it indicates that laser in pulse operation. Another LED displays the laser operation status. Laser has three operation status, warm up, operation, overdrive. When the LED is yellow, it indicates that laser is in warm up status. When the LED is green, it indicates that the system is operational. When the LED is red, it indicates that an overpower adjustment is being made and a protection function has been activated, preventing light from being emitted from the system until the adjustment is complete. The display panel is at an angle position for easy viewing.

A control panel on the enclosure box includes laser power adjustment keys 105a to adjust laser output power. As an example, the laser power could be adjusted in 100 mw intervals. The control panel also includes CW and Pulse operation selection keys 105b, 105c and reset/emergency stop key 105c. When 105a is pushed, laser will be in pulse operation. The pulse rate for one and off time can be 20/80, 40/60, 50/50, 60/40, and 80/20. When 105b is pushed, the laser is in CW operation. In case of emergency, 105c can be pushed to shut off the laser.

A handpiece holder 106 is in the box to hold the handpiece 107 when it is not used. The laser beam on and off can be controlled by a foot switch 108. When the foot switch is pushed, the laser beam will be out, or vice versa.

Figure 1B:
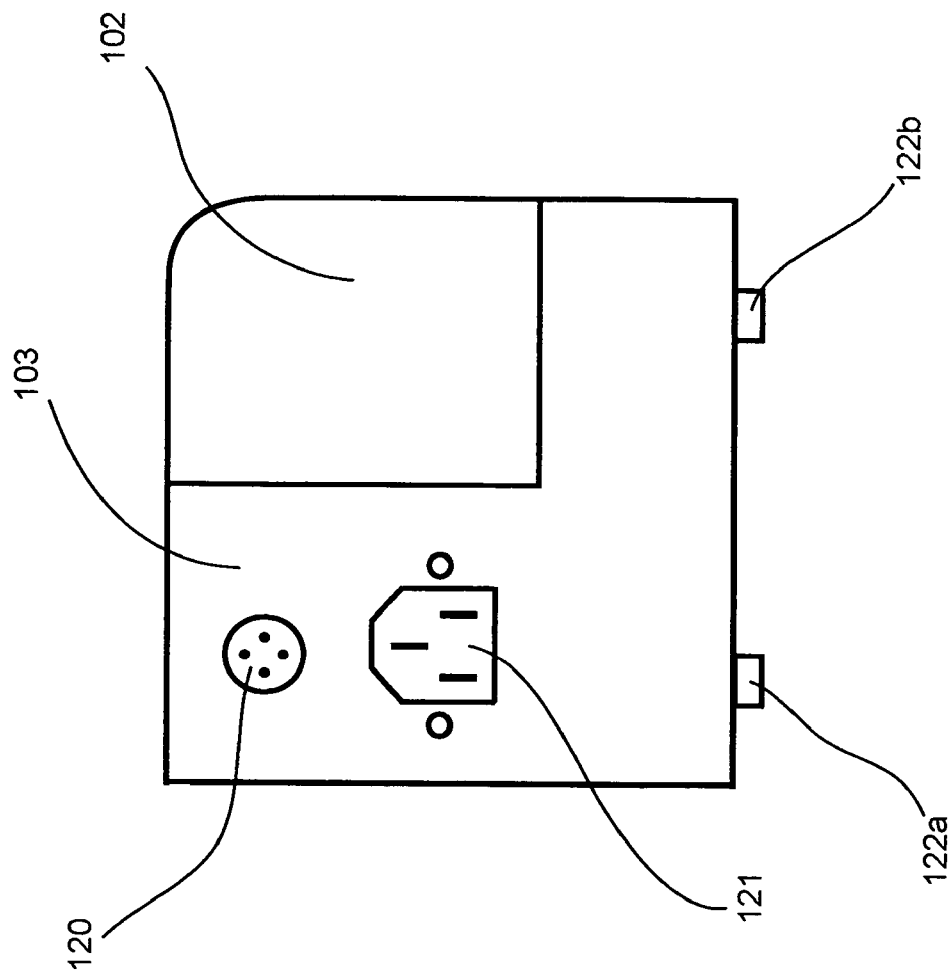

FIG. 1b illustrates the rear panel 103 of the laser system. Part of fiber cartridge 102 can be viewed. The rear panel includes a connector 120 for foot switch. The connector for foot switch can be a two pin, three pin or 4 pin connectors. An electrical power input 121 is in the rear panel for power input. The connector style can be North American, Europe, Asia, and other areas depending on the area of use. The input power for the system can be 90-240V AC 50-60 Hz. FIG. 1b also showed the footings 122a and 122b for laser system. The footing can be rubber or plastic caps to have system stably sitting on the counter.

B. Internal Components and Connections

Figure 1C:
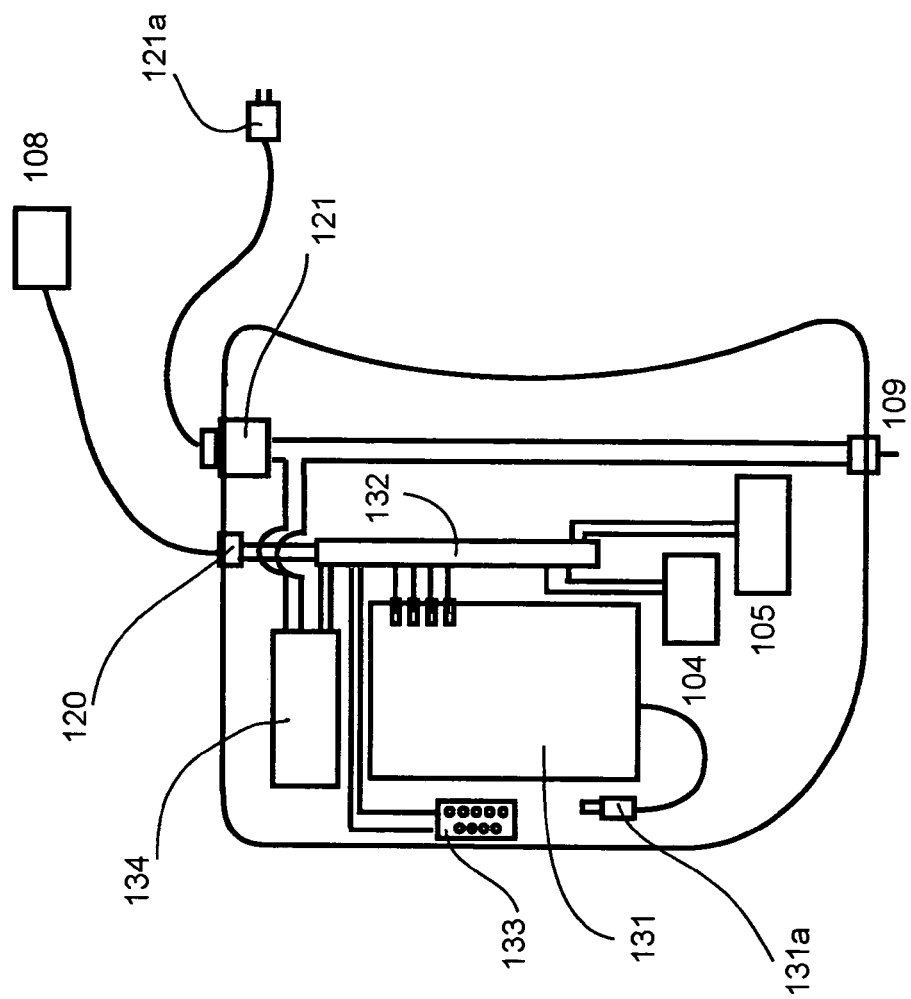

FIG. 1c illustrates the internal components and component connections. The system includes a laser module 131 with a fiber cable and connector 131a. The laser module is connected through electrical conduction wires to a control circuit 132. The control circuit includes the functions to generate a constant DC source for laser operation, to regulate the laser output power, and laser status display. Both laser status display panel 104 as in FIG. 1*a* and control panel 105 as in FIG. 1*a* are connected to the circuit 132. The circuit will also provide control for the fiber cartridge. The control to fiber cartridge is through connector 134. The control circuit also provides connection for foot switch connector 120 as displayed in FIG. 1*b* and foot switch 108 as in FIG. 1*a*. The power for laser operation is provided by a switch power supply 134, which is to convert 90-240 V AC voltage to a desired DC voltage.

C. Fiber Storage and Dispensing Unit

Figure 2A:
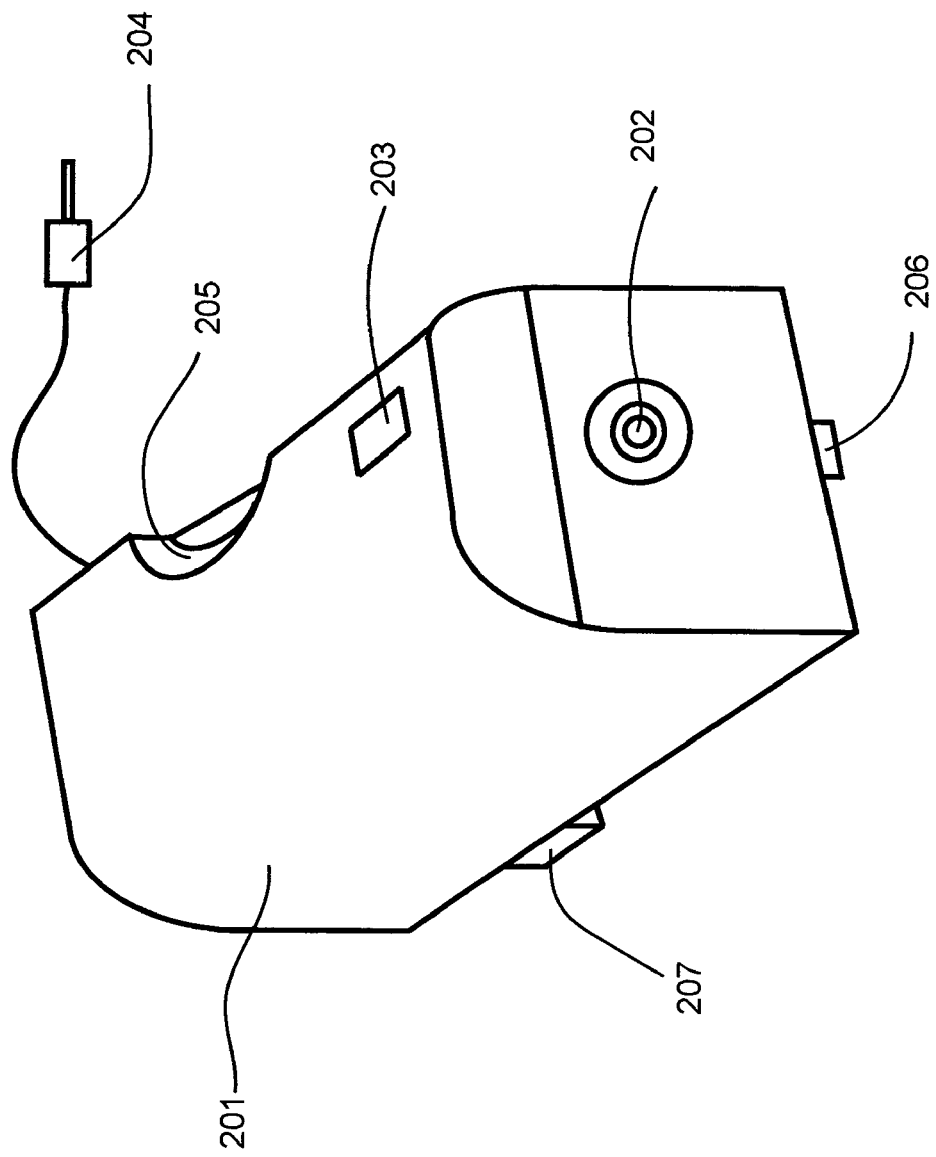
FIG. 2a depicts a fiber cartridge for fiber management
Figure 2B:
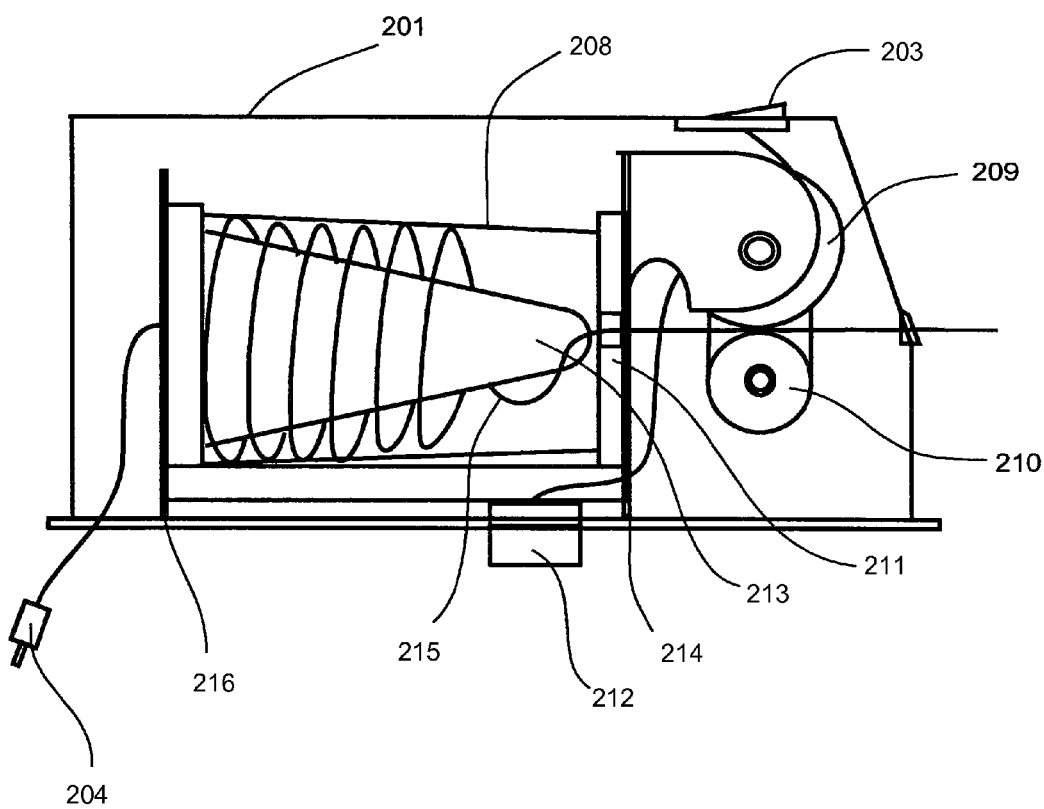
FIG. 2b depicts cross section of fiber cartridge

Referring to FIGS. 2*a* and 2*b*, a fiber storage and dispensing unit is shown. This is the component 102 as displayed in FIG. 1*a*. Fiber storage and dispensing unit 201 may be located in a cavity on the side or front of box 101 with dimensions sufficient for the light transport and dispensing fiber for the laser system. Fiber storage and dispensing unit 201 is a modular unit to storage a certain length of fiber used for application and to dispense the fiber to desired length when it is used.

FIG. 2*a* depicts the exterior of an example of light transport and dispensing unit 201. An outer casing may be provided to protect the interior components of the light transport and dispensing. The outer casing may be made of plastic, metal, alloy or other suitable materials. As light transport and dispensing unit 201 may be a modular unit that is removable and replaceable, and disposable. A fiber outlet 202 is in front section of box 201 to guide the fiber in and out of the cartridge. Outlet 202 may include a perimeter made of plastic or metal and may be a circular, oval, square, or any other desired shape with a diameter sufficient to allow passage of the fiber. A fiber release-retract switch 203 is provided to allow dispensing of a light transporting material such as fiber. Switch 203 may be a push button or toggle switch, moveable knob, or any other switching device. When a user actuates switch 203 in one direction, the motor inside the modular unit 201 extrudes the fiber out of fiber storage. When a user actuates switch 203 in opposite direction, the motor inside the modular unit retracts the fiber into the storage unit. There is a fiber with connector 204 along with the fiber storage. The fiber from the storage is connected through fiber connector 204 to the laser module as in FIG. 1*b*. There is a holder 205 for use to put or remove fiber storage from the enclosure box. There are alignment pins in bottom of the fiber storage cartridge. The alignment pins are used to align the fiber storage in the enclosure box to ensure the storage cartridge is in the same position when being installed. There is a multiple pin connector in the bottom of the fiber storage cartridge for connecting the connector from main control circuit to provide power and control signals. Footings 206 and 207 may be provided.

An interior view of light transport and dispensing unit is shown in FIG. 2*b*. The unit has a casing 201, a fiber storage box 208 in which fiber is stored, a motor control switch 203 for actuating a motor to move fiber out of the box. A motor with wheel 209 and opposing wheel 210 are provided to move fiber out of the fiber storage box 208. A guide 211 is provided for smooth an unimpeded movement of fiber through an aperture in the fiber storage box 208. Within the fiber storage box, there is fiber 215 coiled about a holder 213, which in this case is conical, but which could be cylindrical, tapered or another shape. Braces 214 and 216 serve to retain the fiber storage box 208 in position. A connector 204 is provided to connect to the laser module so that laser light can be transmitted through the fiber to a patient's tissue. An electrical input 212 is provided to power the fiber unit. The fiber unit can include forward and reverse for fiber movement and motor speed control. The fiber unit can be removable and replaceable at relatively low cost.

D. Laser Module

The laser module 301 is an important component in the laser system. FIGS. 3*a*, 3*b*, 3*c* and 3*d* illustrated the invented laser module. Referring FIG. 3*a*, a top view of the module is depicted. The individual laser module has a casing 301. The casing may be made of Al alloys, plastic, metals and other materials. The module has an fiber outlet 302 and a fiber cable 303 with connector 304. On side of the module, there are 4 connectors 305*a*, 305*b*, 305*c* and 305*d*. Two of electrical connectors 305*a* and 305*b* are used to connect an electrical signal from the electric control circuit (discuss below) to the semiconductor laser chip inside the module and two of the connectors 305*c* and 305*d* are used to receive the electrical signal from photodetector inside the module. The laser output power is controlled by detecting the signal from the photodetector. Detailed laser module operation mechanism is described in section below.

Figure 3A:
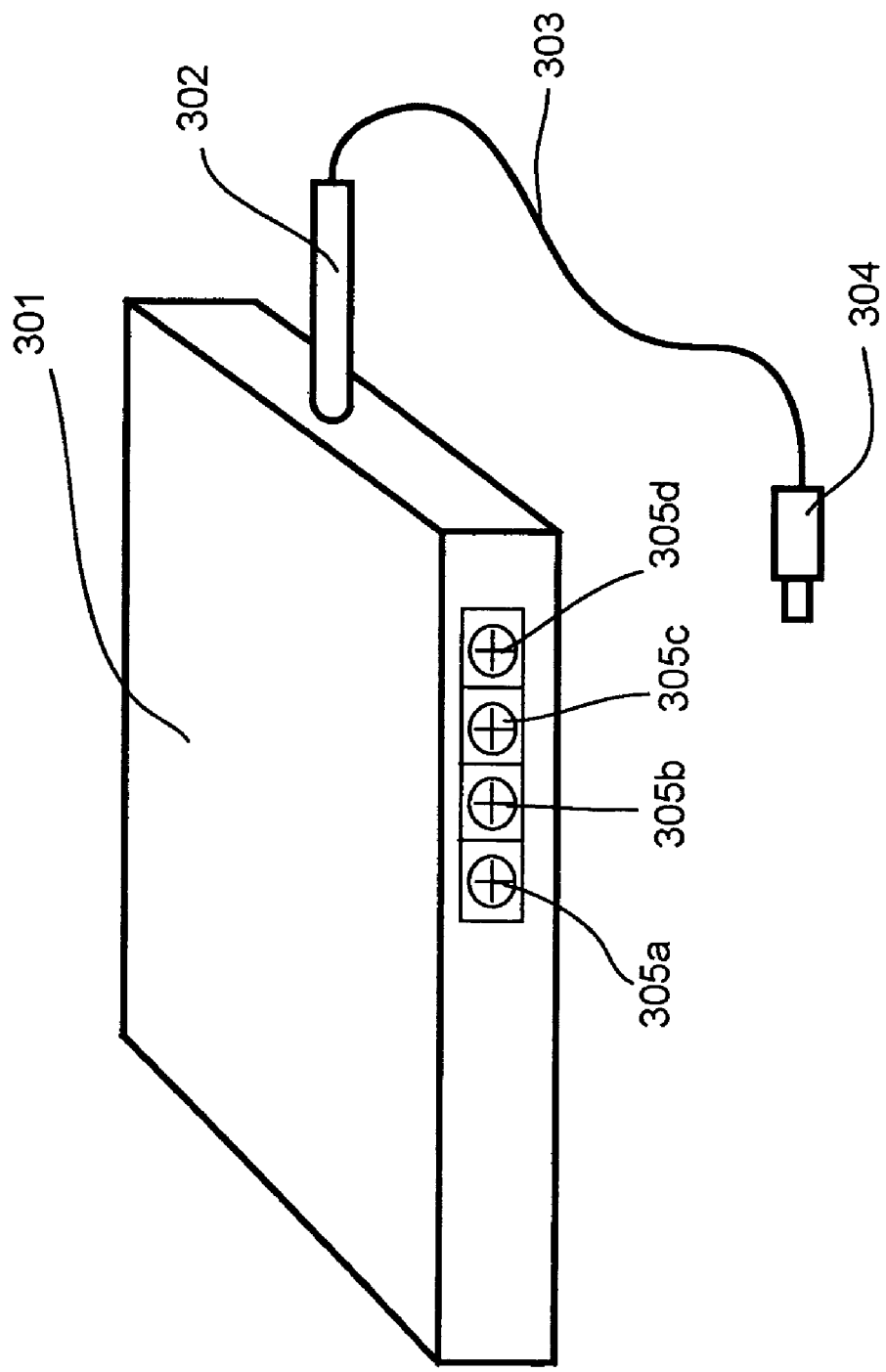
FIG. 3a depicts the laser module used in the laser system
Figure 3B:
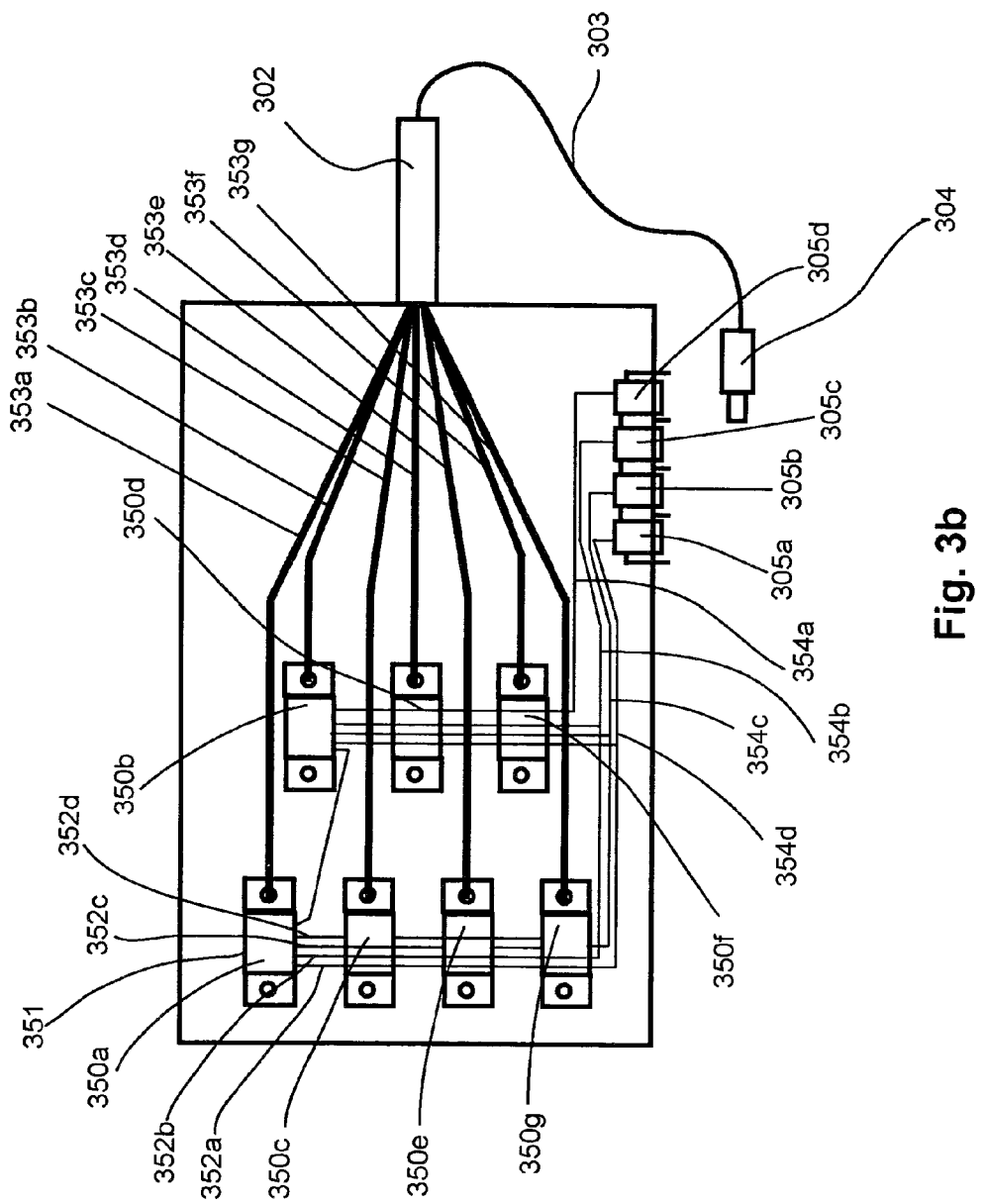
FIG. 3b depicts the inside arrangement of laser module
Figure 3C:
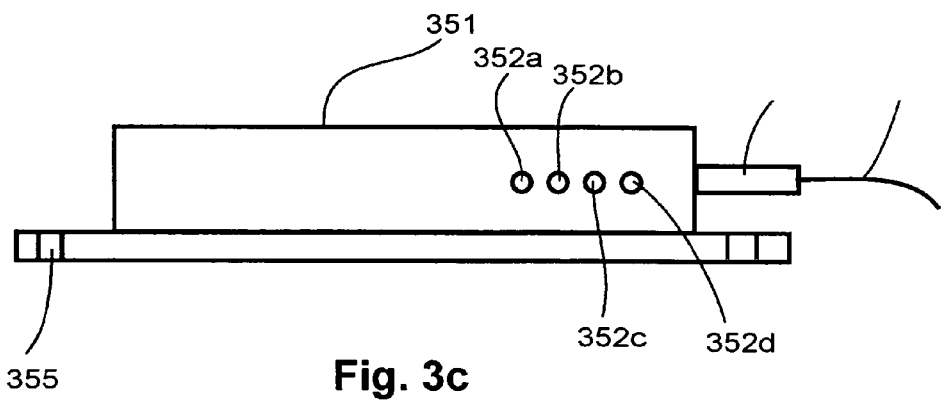
FIG. 3c depicts the individual laser module

FIG. 3*b* depicts the inside components and diagram of laser module. Inside the laser module, there is a number of individual laser modules 350*a*, 350*b* and etc. 7 individual modules are illustrated in FIG. 3*b*. The individual module is depicted in FIG. 3*c*. Each individual module has a casing 351, and 4 electrodes, 352*a*, 352*b*, 352*c* and 352*d*, and a fiber outlet (360 in FIGS. 3*c* and 3*d*) and a fiber 353*a*, 353*b*, 353*c*, etc. The electrodes 352*a* and 352*b* is signal from photodetectors and 352*c* and 352*d* are for input power for laser chip. There is a base on casing 351 with holes 355*a*, 355*b*, 355*c* and 355*d*. The individual module is attached to the laser module casing using holes 355*a*, 355*b*, 355*c* and 355*d* or heat conductive adhesives. Use of photodectors permits feedback to the control circuit to manage laser power output levels. Connection wires 354*a*, 354*b*, 354*c*, etc. connect each module to electrical connectors 305*a*, 305*b*, 305*c* and 305*d*. FIG. 3*c* depicts a side view of the laser unit 351.

Figure 3D:
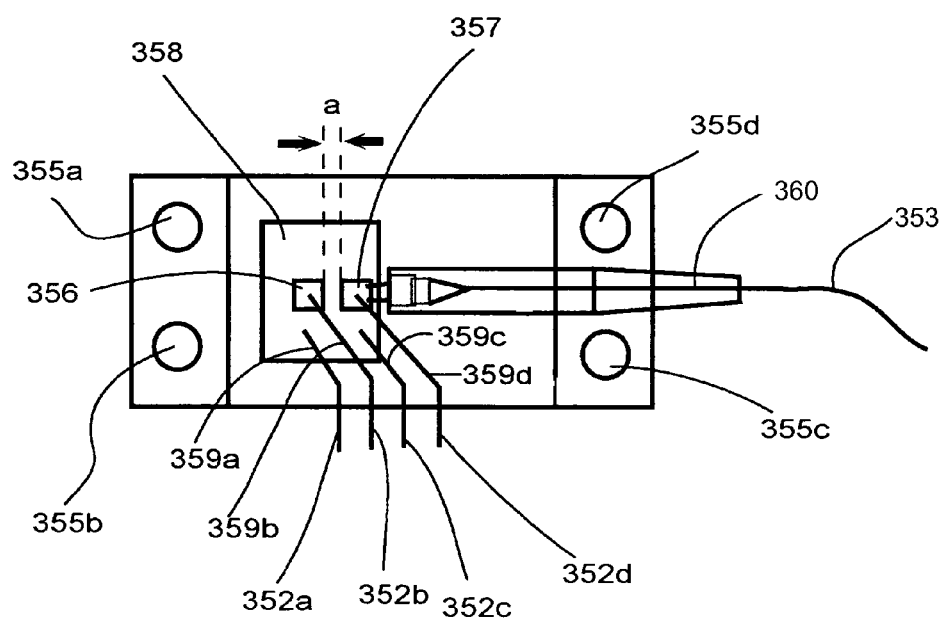
FIG. 3d depicts the inside of individual laser module

FIG. 3*d* depicts the arrangement of laser chip and photodetector inside the individual laser module. The photodetector chip 356 and laser chip 357 are mounted on a heat sink 358 using heat and electrical conductive materials. The heat sink is directly mounted to the casing of the individual module. The electrical wires, i.e. gold wires, 359*a*, 359*b*, 359*c*, and 359*d* are attached to the heat sink 358, chips 356, 357 and electrodes 352*a*, 325*b*, 352*c*, 352*d* in the casing respectively to make electrical connections. The photodetector chip 356 is mounted right behind of the laser chip 357 to monitor the laser power output. The photodetector's primary function as described above is to convert light into an electric signal for communication with the electric control module, although other uses may also be possible. The light emitted from laser is collected by an optical coupler. The heat sink 358 and fiber outlet 360 collect light from individual chip 357, and focus the light into a small beam and into the fiber 353.

E. Fiber Coupling

Figure 4A:
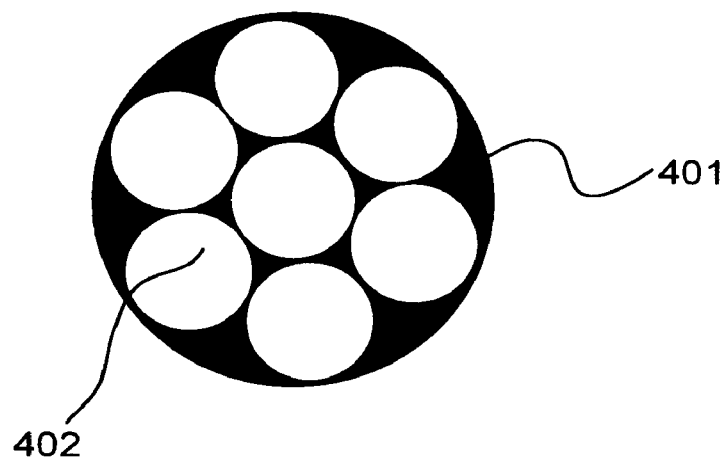
FIG. 4a depicts the fiber arrangement for laser module

The laser beam from the laser beam module needs to be coupled to the fiber cartridge for light transmission therethrough to a patient. The fiber from the laser is bundled. The fiber in the fiber cartridge is a single fiber. There are several methods to couple the laser beam from the laser module to the fiber cartridge. FIG. 4*a* illustrates a cross section of fiber bundle from the laser module inside a fiber connector. The circumferential diameter 401 is a diameter of fiber connector and 402 is diameter of individual connector. Seven individual fibers impacted inside the connector is illustrated in FIG. 4*a*.

Figure 4B:
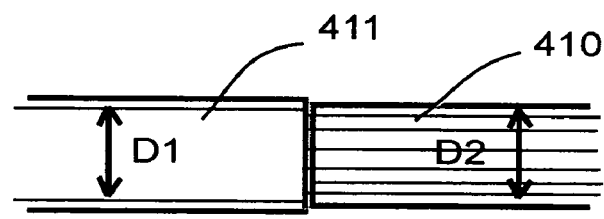
FIG. 4b depicts one of the fiber coupling mechanisms, bundling multiple fibers into an individual fiber.

FIG. 4*b* depicts one of coupling mechanism from a fiber bundle 410 to an individual fiber 411. In order to achieve the good fiber coupling, the diameter D1 of single fiber 411 is preferred to larger than overall diameter D2 of fiber bundle 410. Both fibers are needed to be polished and closely contacted.

Figure 4C:
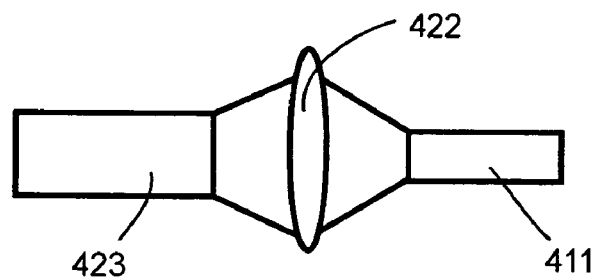
FIG. 4c depicts one of the fiber coupling mechanisms, bundling multiple fibers into an individual fiber.

FIG. 4c depicts another of coupling mechanism from a fiber bundle 423 to a single fiber 411. In this mechanism, a optical lens 422 is used to focus the beam from fiber bundle to single fiber.

F. Electric Control Module

Figure 5:
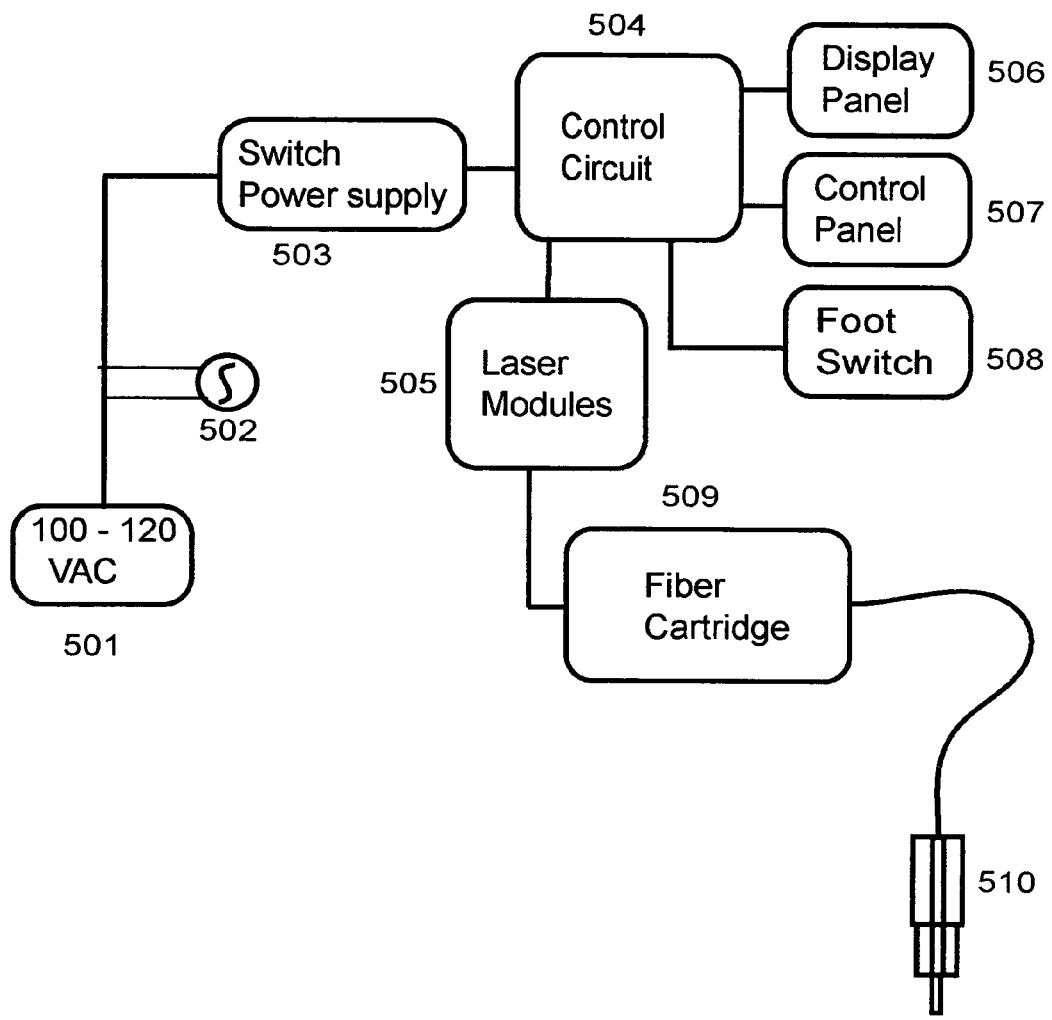
FIG. 5 depicts the electrical control diagram of the laser system.

Referring to FIG. 5, an example electric control module is depicted in greater detail. The electronic control module provides electrical regulation and laser beam control for the laser system.

A 110 or 220-volt AC source 501 may be supplied from a standard wall outlet. Key switch 502 (if used) must be turned on for current to flow into the switch power supply 503 to supply the proper power level to the module and supplies power to the control circuit 504. The control circuit 504 may be provided to control the supply of electric current to the laser module 505. The display panel 506, control panel 507, and food switch 508 are all connected to control circuit. The fiber from the laser module is coupled into fiber cartridge 509, then used for operation through a hand piece 510.

G. Hand Piece for Surgery and Therapeutic

Figure 6A:
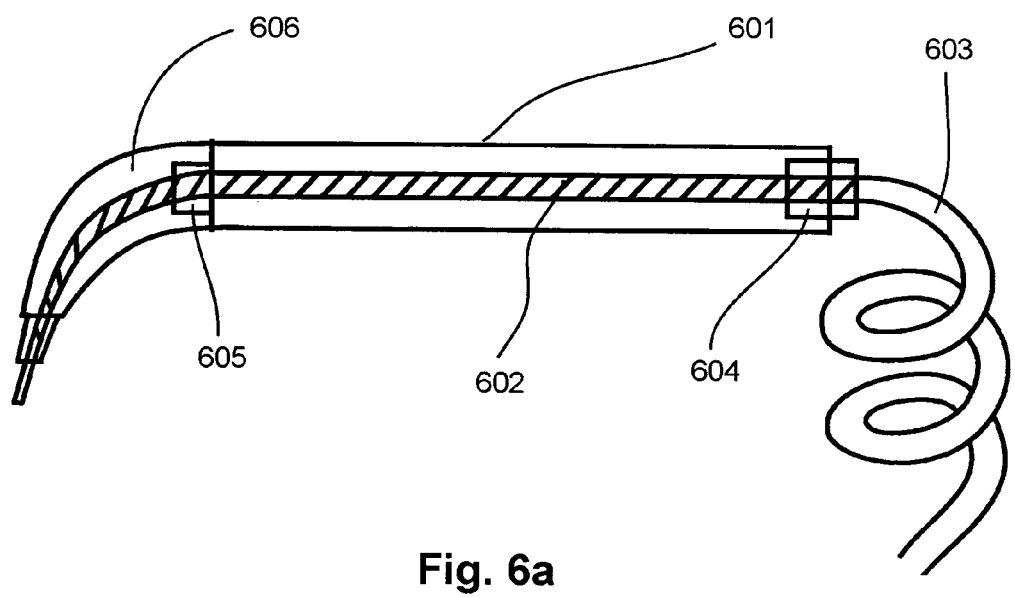
FIG. 6a depicts an example laser handpiece.
Figure 6B:
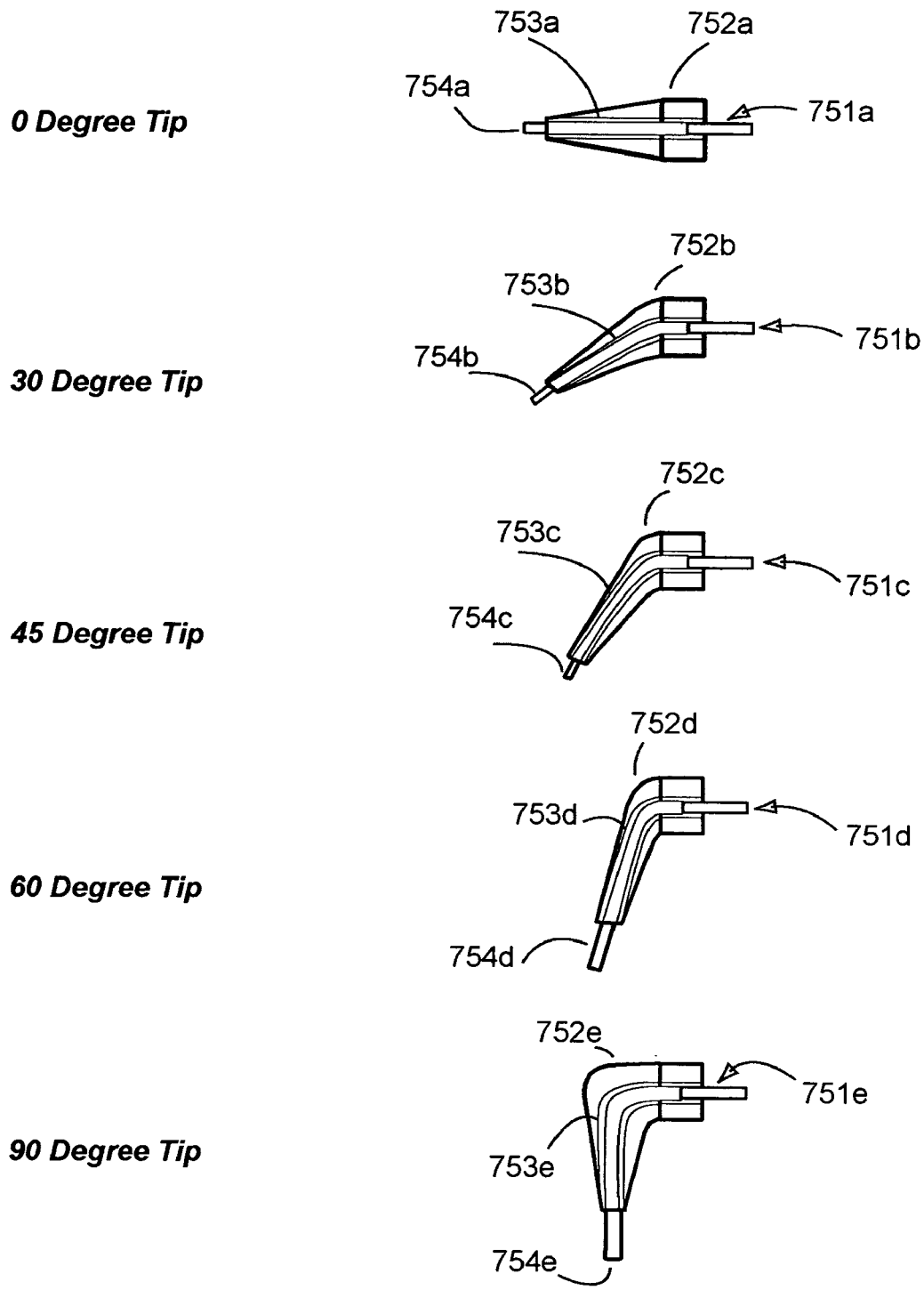
FIG. 6b depicts example handpiece tips.

Referring to FIG. 6a, a side view of operation hand piece 601 is shown. The hand piece serves to control the fiber which delivers a laser beam to a therapeutic or surgical surface. The handpiece may be ergonomically designed to ensure a firm grip, user comfort, and maximum manual dexterity and maneuverability during use and is made of plastic or any other suitable material. The hand piece 601 includes a channel 602 to guide the fiber 603 from the fiber cartridge through the hand piece. There is a stopper 604 in the rear end of the hand piece to hold the fiber steady. On the other side of handpiece, there is connector 605 to fit to a laser tip 606. The fiber 603 passes through tip to deliver the laser beam. The tip 606 is removable from the hand piece. The tip 606 may have various desired angles as depicted in FIG. 6b. The tip can have 0, 30, 45, 60, 90 degree angles (or otherwise) to the longitudinal axis of the fiber running through the handpiece. Referring to FIG. 6b, a fiber 751a, 751b, 751c, etc., passes through a tip 752a, 752b, etc., which has a distal end 753a, 753b, etc. angled with respect to the longitudinal axis of the fiber as it enters the tip to present a distal fiber end 754a, 754b, 754c, etc., which may emit light that is at an angle to the direction of light traveling through the fiber within the handpiece.

H. Setup for Therapeutic Applications

Figure 7:
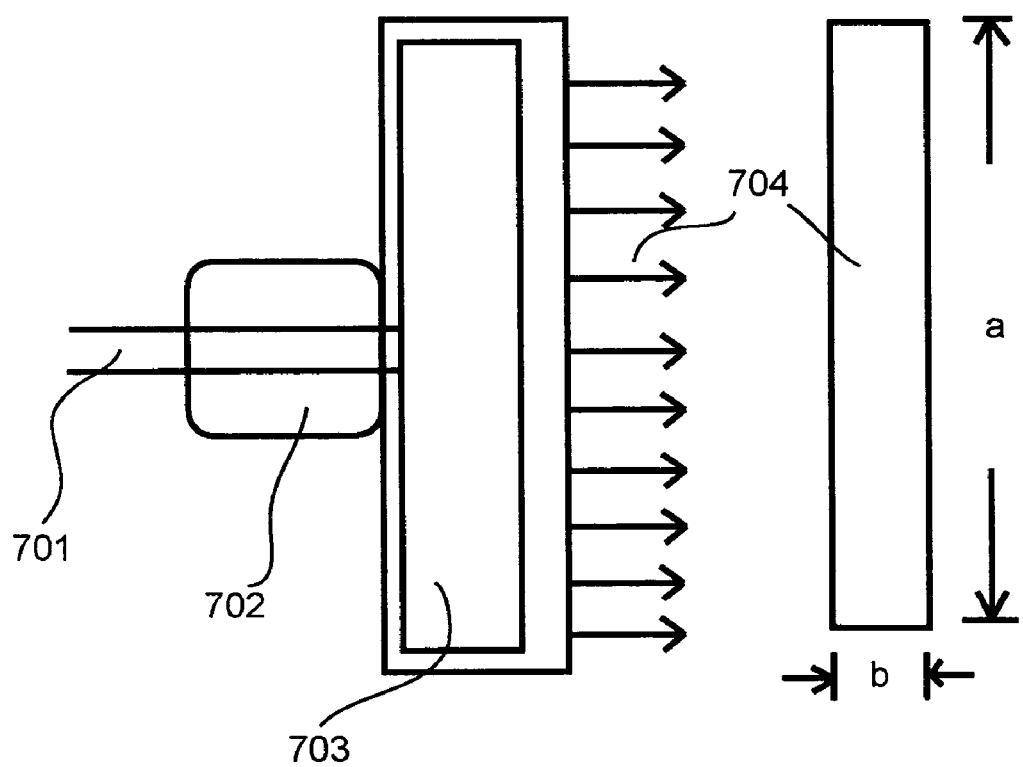
FIG. 7 depicts a method to produce a bar beam of light from a single fiber.

In therapeutic and dermatology treatment, it may be desired to have a large beam size delivered to the treatment surface other than small spot. FIG. 7 depicts a setup to produce a large beam by adopting the single fiber from fiber cartridge to an optical setup. The single fiber 701 from fiber cartridge is connected through a handle 702 to the a cylindrical or rectangular lens 703, which will converts the single spot beam to a large size beam 704, which may have nearly any shape but in this example is rectangular with dimensions a×b. The size of the laser beam footprint can be as desired, such as from 1 mm to 100 mm, or 1 to 50 mm, or otherwise.

I. Setup for Tooth Whitening

Figure 8A:
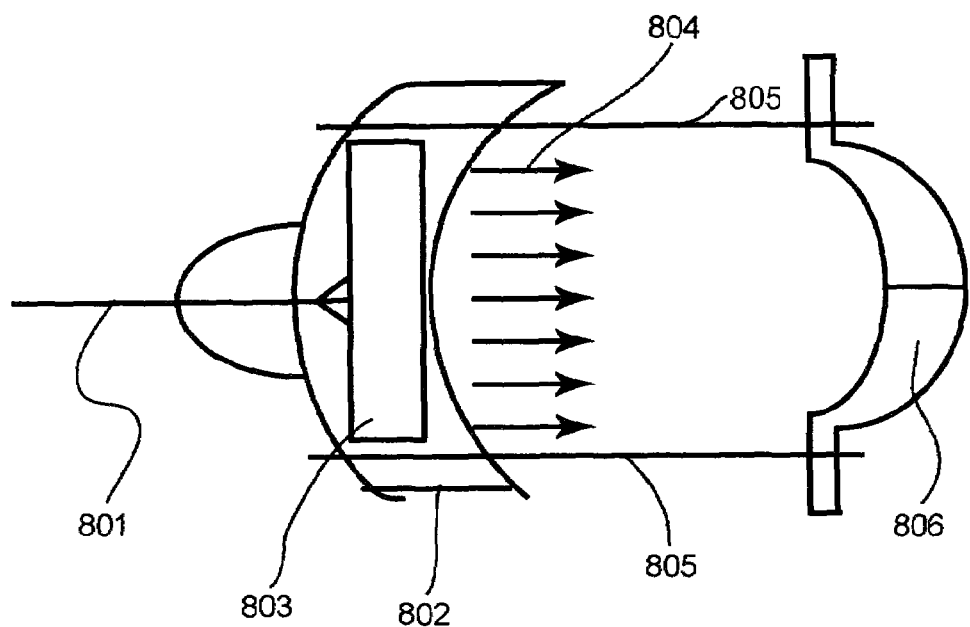
FIG. 8a depicts a setup for teeth whitening.
Figure 8B:
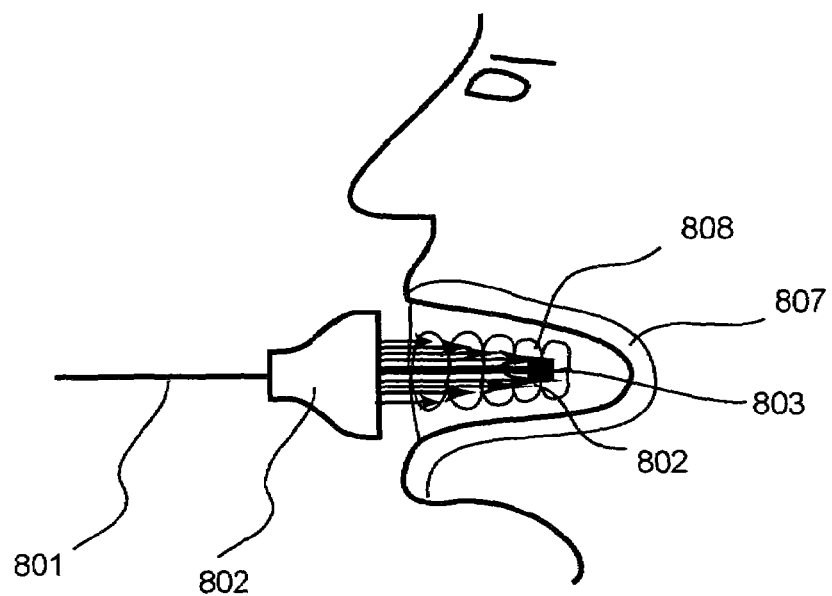
FIG. 8b depicts whitening teeth with a laser.

The laser can also be used for tooth whitening. FIGS. 8a and 8b depict the setup of tooth whitening using laser system described above. FIG. 8a illustrates the whitening setup. A single fiber 801 from the fiber cartridge is attached to a whitening module 802 including a cylindrical lens 803. The cylindrical lens converts the single spot laser beam to a nearly rectangular beam 804. The whitening module 802 is attached to a tongue holder 806 through 2 rigid wires 805. The distance between tong holder 806 and light module 802 can be adjusted. FIG. 8b illustrates the application method for tooth whitening. The patient's lips 807 are opened by a dental setup to have teeth 808 exposed. The patient then bites the tongue holder to hold the light module 802 right in front of the teeth. The laser beam can be directly shinning on the surface of the teeth. The beam size of laser light can be adjusted to fit the dimensions of the patient's teeth area.

While laser systems and their structures have been described and illustrated in conjunction with a number of specific configurations herein, those skilled in the art will appreciate that variations and modifications may be made without departing from the principles herein illustrated, described, and claimed. The present invention, as defined by the appended claims, may be embodied in other specific forms without departing from its spirit or essential characteristics. The configurations of laser devices described herein are to be considered in all respects as only illustrative, and not restrictive. All changes which come within the meaning and range of equivalency of the claims are to be embraced within their scope.

I claim:

1. A laser system useful in medicine or dentistry comprising:
   a housing,
   a laser module within said housing, said laser module being capable of producing laser light which is usable for therapeutic purposes in medicine or dentistry,
   a fiber module, said fiber module having an outer casing attachable to and removable from said housing and configured to store amounts of extra fiber,
   said fiber module including fiber therein, said fiber having a proximal end and a distal end, and
   said fiber proximal end being in light communication with said laser module so that said fiber can receive laser light from said laser module and transport said laser light to said fiber distal end.

2. A laser system as recited in claim 1 wherein said fiber module includes a fiber holder.

3. A laser system as recited in claim 2 wherein said fiber holder is conical in shape.

4. A laser system as recited in claim 2 wherein said fiber holder is cylindrical in shape.

5. A laser system as recited in claim 2 wherein said fiber holder has a tapered shape.

6. A laser system as recited in claim 2 further comprising an electrically powered motor for moving fiber from within said fiber module to the exterior of said fiber module.

7. A laser system as recited in claim 6 wherein said motor includes speed control for increasing or decreasing the speed with which fiber may be removed from said fiber module.

8. A laser system as recited in claim 6 further comprising a first wheel and a second wheel, said first wheel being powered by said motor and said second wheel permitting said fiber to move thereagainst when said first wheel turns in an attempt to move fiber outside of said housing.

9. A laser system as recited in claim 6 wherein said motor has a forward function and a reverse function so that it can move fiber both out of and into said fiber module.

10. A laser system as recited in claim 1 wherein said fiber module is disposable when substantially of the fiber within it has been depleted.

11. A therapeutic laser system useful in medicine or dentistry comprising:
   a casing,
   a laser module capable of producing laser light which is usable for therapeutic purposes in medicine or dentistry,
   a fiber storage module, further comprising a module housing attachable and detachable from the casing and having a volume sufficient to store significant amounts of extra fiber, fiber, mostly stored in the fiber module but at least some fiber being located in said casing, and a distal end of said fiber projecting from within said casing to the exterior of said casing, said fiber having a proximal end, and said fiber proximal end being in light communication with said laser module so that said fiber can receive laser light from said laser module and transport said laser light to said fiber distal end, further comprising a handpiece adapted to receive said fiber distal end and being adapted for gripping by a human hand.

12. A laser system as recited in claim 11 wherein said fiber module includes a fiber holder.

13. A laser system as recited in claim 12 wherein said fiber holder is conical in shape.

14. A laser system as recited in claim 12 wherein said fiber holder is cylindrical in shape.

15. A laser system as recited in claim 12 wherein said fiber holder has a tapered shape.

16. A laser system as recited in claim 12 further comprising an electrically powered motor for moving fiber from within said fiber module to the exterior of said fiber module.

17. A laser system as recited in claim 16 wherein said motor includes speed control for increasing or decreasing the speed with which fiber may be removed from said fiber module.

18. A laser system as recited in claim 16 further comprising a first wheel and a second wheel, said first wheel being powered by said motor and said second wheel permitting said fiber to move thereagainst when said first wheel turns in an attempt to move fiber outside of said casing.

19. A laser system as recited in claim 16 wherein said motor has a forward function and a reverse function so that it can move fiber both out of and into said fiber module.

20. A laser system as recited in claim 11 wherein said fiber module is disposable when substantially of the fiber within it has been depleted.

21. A laser system as recited in claim 11 further comprising a fiber tip, said fiber tip being attachable to said handpiece and optically coupled to said fiber distal end, said fiber tip serving to determine angular orientation of laser light emitted by said fiber distal end with respect to said handpiece.

* * * * *